United States Patent [19]

Fremont

[11] 4,110,249

[45] Aug. 29, 1978

[54] PREPARATION OF BISMUTH MODIFIED SPHEROIDAL MALACHITE

[75] Inventor: Joseph Melvin Fremont, Glen Mills, Pa.

[73] Assignee: E. I. Du Pont de Nemours and Company, Wilmington, Del.

[21] Appl. No.: 803,261

[22] Filed: Jun. 6, 1977

Related U.S. Application Data

[63] Continuation-in-part of Ser. No. 711,724, Aug. 5, 1976, abandoned.

[51] Int. Cl.$^2$ .............................................. B01J 27/20
[52] U.S. Cl. .................................. 252/431 R; 252/443; 568/855

[58] Field of Search ........................... 252/431 R, 443; 260/635 Y

[56] References Cited

U.S. PATENT DOCUMENTS

| | | | |
|---|---|---|---|
| 2,300,969 | 11/1942 | Reppe et al. | 252/431 R X |
| 3,650,985 | 3/1972 | Kirchner | 252/431 R |

*Primary Examiner*—Patrick P. Garvin

[57] ABSTRACT

Spheroidal agglomerates of malachite crystals are prepared by bringing together solutions of a cupric salt, a bismuth salt and an alkali metal carbonate or bicarbonate to form a mixture containing amorphous hydrated copper carbonate, and then holding the mixture, without agitation, at a temperature of less than about 55° C.

8 Claims, No Drawings

PREPARATION OF BISMUTH MODIFIED SPHEROIDAL MALACHITE

CROSS REFERENCE TO RELATED APPLICATION

This application is a continuation-in-part of application Ser. No. 711,724, filed Aug. 5, 1976, now abandoned.

BACKGROUND AND SUMMARY OF THE INVENTION

The method of producing 1,4-butynediol by the reaction of formaldehyde and acetylene using a copper acetylide complex as a catalyst is, of course, well known and has been used for many years. It is also well known that this reaction produces cuprene, which tends to clog filters and affects the process adversely.

One method commonly used to inhibit cuprene formation during the reaction is to conduct it in the presence of bismuth, either in elemental form or in the form of a bismuth compound. In Kirchner U.S. Pat. No. 3,650,985, for example, it is demonstrated in Example 39 that bismuth oxycarbonate can be used as a cuprene inhibitor by mixing it, in the initial stage of the process, directly with the basic copper carbonate (malachite) used to form the copper acetylide catalyst. While bismuth used in this way does inhibit cuprene formation, it tends to separate from the catalyst after a time, which leads to unsatisfactory results.

One method of dealing with the separation of bismuth from the catalyst is shown in Belgian Pat. 825,446, according to which bismuth is uniformly dispersed in a malachite precursor, and subsequently in the copper acetylide catalyst itself, by first preparing hydrated copper carbonate particles, nucleating and converting these particles to malachite by heating them, and then growing agglomerates of malachite containing bismuth oxycarbonate uniformly dispersed therein by adding solutions of a copper salt, a bismuth salt and an alkali metal carbonate to a water slurry of the malachite. This malachite is easily converted to a copper acetylide catalyst.

While the bismuth compound in a catalyst thus produced tends to stay in place, the catalyst is composed of agglomerates of angular crystals which are degraded by attrition as the butynediol reaction proceeds, which interferes with its efficiency.

This problem, as well as the others just mentioned, is minimized by the use of the malachite and copper acetylide catalyst produced according to this invention, whose agglomerates are spheroidal and contain uniformly dispersed bismuth oxycarbonate.

The spheroidal agglomerates of malachite can be made according to the invention by first forming a mass of hydrated copper carbonate by bringing together, with mixing, an aqueous solution of a cupric salt, an aqueous solution of a bismuth salt and an aqueous solution of an alkali metal carbonate or bicarbonate. This mixture is then held, without stirring or agitation, at a temperature of less than about 55° C, whereupon the spheroidal agglomerates of malachite crystals form.

These agglomerates can, in turn, be converted to copper acetylide complex by slurrying them in water and then subjecting them to the action of acetylene and formaldehyde.

DETAILED DESCRIPTION OF THE INVENTION

Any water soluble cupric salt can be used in the process of the invention. Illustrative are cupric nitrate, cupric chloride and cupric sulfate. Cupric nitrate is preferred because of its solubility and availability.

Similarly, any water soluble bismuth salt can be used. Illustrative are the nitrate, the oxycarbonate, the citrate, the sulfate and the phosphate. Bismuth nitrate is preferred, also because of its solubility and availability.

Of the alkali metal carbonates and bicarbonates which can be used, sodium carbonate and sodium bicarbonate are preferred because of their low cost.

Each salt solution is prepared so that it contains as much salt as possible without it crystallizing from solution on standing or during use. The solutions are then brought together in such proportions that the pH of the resulting mixture is about 5.5 to about 7.5, preferably 6.0 to 7.0. In the usual case, this pH range can be attained by the use of an appropriate amount of the alkali metal carbonate or bicarbonate solution. The bismuth salt is usually present in the resulting mixture at a concentration of 1 to 10%, by weight, of the copper content.

The solutions can be brought together in any order, generally over a period of 20 to 60 minutes, and are then mixed by stirring or by agitation. In a preferred embodiment, a solution of the copper salt and the bismuth salt is prepared, and this is fed to a small heel of water, simultaneously with a solution of the alkali metal carbonate or bicarbonate, as shown in Example 1.

It is important that the solutions be brought together in a vessel which has been cleansed of malachite nuclei by first rinsing it with dilute nitric acid.

The resulting mixture is held at a temperature of just slightly above the freezing point of the medium to about 55° C, preferably 35° C, to 50° C, with stirring or agitation. An amorphous mass of gel-like hydrated copper carbonate forms immediately.

The agglomerates of malachite are then prepared from the hydrated copper carbonate by holding the liquid in which the carbonate is contained at about the same temperature as is used in the gel-formation step, without stirring or agitation of any kind. Carbon dioxide begins to evolve and agglomerates of malachite crystals form. Formation is ordinarily complete in about 1 to 3 hours.

The malachite thus formed consists of spheroidal agglomerates of basic copper carbonate crystals. At least about 80% of these agglomerates are about 5 to 12 microns in the longest dimension, as determined optically against a standard. The agglomerates contain 1 to 4%, by weight, of uniformly dispersed bismuth oxycarbonate, preferably 2 to 3%. "Uniformly dispersed" means the oxycarbonate is evenly distributed through all of the agglomerate on a molecular scale.

The agglomerates are then separated from the reaction mass by filtration, and washed free of salts with water. When higher concentrations of bismuth salt are used in preparing the agglomerates, it is desirable that residual gel and smaller agglomerates be removed by hydrocloning the reaction mixture before the filtration step. A suitable apparatus for this step is the Dorr Clone, made by Dorr-Oliver, Inc., of Stamford, Connecticut.

These malachite agglomerates can be converted into copper acetylide catalyst by preparing a slurry of agglomerates in water and then subjecting this slurry to the action of acetylene and formaldehyde. This procedure is described in more detail in Kirchner, U.S. Pat. No. 3,650,985, beginning in column 5. The portions of the Kirchner patent which describe the procedure are incorporated into this application by reference.

The copper acetylide complex produced in this way is in the form of spheroidal agglomerates containing uniformly dispersed bismuth oxycarbonate, at concentrations which parallel that of the malachite from which the complex is prepared.

The complex can be used as a catalyst for the reaction of acetylene and formaldehyde to produce 1,4-butynediol. The complex is used in the customary way and in the usual amounts, and no special techniques or precautions are necessary. Details for such use can be found in Kirchner U.S. Pat. No. 3,650,985.

EXAMPLES

EXAMPLE 1

In 100 ml of water were dissolved
$Cu(NO_3)_2 \cdot 3H_2O$ — 95 g
Concentrated $HNO_3$ — 10 ml
$Bi(NO_3)_3 \cdot 5H_2O$ — 1.74 g The resulting solution was fed, with stirring, over a 40 minute period, to 300 ml of water held at 35° C. Enough saturated aqueous solution of $Na_2CO_3$ was added to keep the pH of the solution at 6.7 to 7.2

Stirring was then stopped and the solution held at 35° C. A blue gel filled the vessel; this gel contracted to ½ its original volume in about 2½ hours to form spherical agglomerates of malachite crystals, which were then separated from the liquid by filtration, washed with water and then dried at 100° C. for 1 hour. This product was then hydrocloned to remove residual gel and small particles.

At least 80% of these agglomerates were 5 to 12 microns in the longest dimension.

EXAMPLE 2

To a glass vessel were charged
Malachite of Example 1 — 45 g
Formaldehyde (37% in — 600 g water
$CaCO_3$ — 2 g A stream of acetylene containing 90% by volume of nitrogen was passed through the vessel at a rate of 2 liters/minute. The pressure within the vessel was held at 4 to 5 psig and the temperature of the reaction mass at 70° to 80° C. The carbon dioxide which formed was vented to the outside.

When carbon dioxide evolution stopped, the contents of the vessel were cooled, removed from the vessel and washed with water.

The resulting copper acetylide complex was stored under water until ready for use.

EXAMPLE 3

To a reactor vessel were charged
Copper-acetylide complex — 45 g of Example 2
Formaldehyde (15% in — 600 ml water)

Acetylene was continuously passed through the vessel at a rate of 300 ml/minute, the pressure being maintained at about 5 psig. Enough of a 37% aqueous solution of fomaldehyde was continuously fed into the vessel to maintain a formaldehyde concentration of about 10% by weight. Similarly, enough of a saturated solution of sodium bicarbonate was continuously fed into the vessel to hold the pH of the contents at 6.0 to 6.2. The product, 1,4-butynediol, was continuously removed by filtration.

After 100 hours of continuous use, the catalyst was removed from the vessel and analyzed by X-ray diffraction scanning. No metallic copper was detected, indicating that the catalyst remained stable and useful.

EXAMPLE 4

The process of Example 1 was repeated, using 5.8 g of bismuth nitrate instead of 1.74 g.

The resulting spheroidal agglomerates of malachite contained 4%, by weight, of uniformly dispersed bismuth oxycarbonate.

These agglomerates can be converted to copper acetylide catalyst as shown in Example 2, which in turn can be used in the procedure shown in Example 3 to form 1,4-butynediol.

I claim:

1. A process for producing spheroidal agglomerates of basic copper carbonate crystals, at least about 80% of the agglomerates being 5 to 12 microns in the longest dimension, the agglomerates containing 1 to 4% by weight of bismuth oxycarbonate, the process consisting essentially of
    (A) forming amorphous gel-like hydrated copper carbonate by bringing together in aqueous solution with mixing, at a temperature less than about 55° C, enough of
        (1) a cupric salt,
        (2) a bismuth salt, and
        (3) an alkali metal carbonate or an alkali metal bicarbonate, to yield a mixture with a pH value of 5.5 to 7.5; and then
    (B) holding the mixture of (A), without agitation, at a temperature less than about 55° C, until the spheroidal agglomerates are formed.

2. The process of claim 1 in which the cupric salt is cupric nitrate, the bismuth salt is bismuth nitrate and the alkali metal carbonate is sodium carbonate.

3. The process of claim 1 in which the temperature in steps (A) and (B) are 35° to 50° C.

4. A spheroidal agglomerate of basic copper carbonate crystals, produced by the process of claim 1.

5. A spheroidal agglomerate of basic copper carbonate crystals, produced by the process of claim 2.

6. A process for the formation of a copper acetylide complex, the process consisting essentially of subjecting the product of claim 4, as a slurry in an aqueous medium, to the action of formaldehyde and acetylene.

7. A process for the formation of a copper acetylide complex, the process consisting essentially of subjecting the product of claim 5, as a slurry in an aqueous medium, to the action of formaldehyde and acetylene.

8. The copper acetylide complex produced by the process of claim 6.

* * * * *